United States Patent [19]

Sasaki et al.

[11] Patent Number: 4,598,092

[45] Date of Patent: Jul. 1, 1986

[54] α-HYDROXY-β-HALOETHYLPHOSPHINIC ACIDS AND THEIR SALTS, AND THEIR PRODUCTION AND USE

[75] Inventors: Mitsuru Sasaki; Yukio Oguri, both of Toyonaka, Japan

[73] Assignee: Sumitomo Chemical Company, Limited, Osaka, Japan

[21] Appl. No.: 553,049

[22] Filed: Nov. 18, 1983

[30] Foreign Application Priority Data

Dec. 1, 1982 [JP] Japan ................... 57-211815

[51] Int. Cl.$^4$ .................. C07F 5/06; A01N 55/02; A61K 31/28

[52] U.S. Cl. .................... 514/492; 514/140; 514/493; 514/494; 514/499; 514/501; 514/502; 556/19; 556/174

[58] Field of Search .............. 260/970, 961, 429 R, 260/429.9, 439 R, 448 R, 438.1, 429.7, 429.5; 556/19, 174; 514/140, 492, 493, 494, 499, 501, 502

[56] References Cited

U.S. PATENT DOCUMENTS

| | | | |
|---|---|---|---|
| 2,579,810 | 12/1951 | Fields | 260/970 |
| 2,701,225 | 2/1955 | Lorenz | 260/970 X |
| 2,951,086 | 8/1960 | Chadwick | 260/961 X |
| 2,962,518 | 11/1960 | Lorenz et al. | 260/970 X |
| 3,070,489 | 12/1962 | Newallis et al. | 260/970 X |
| 3,280,131 | 10/1966 | Wakeman et al. | |
| 3,407,248 | 10/1968 | Klauke et al. | 260/970 X |
| 3,626,037 | 12/1971 | Randall et al. | 260/961 |
| 4,431,596 | 2/1984 | Tsolis et al. | 260/970 |

FOREIGN PATENT DOCUMENTS 0063464 10/1982 European Pat. Off. .
0093010 2/1983 European Pat. Off. .

OTHER PUBLICATIONS

Kosolapoff, Organophosphorus Compounds, John Wiley & Sons, Inc. N.Y. pp. 129–130 (1950).

Primary Examiner—Helen M. S. Sneed
Attorney, Agent, or Firm—Birch, Stewart, Kolasch & Birch

[57] ABSTRACT

A compound of the formula:

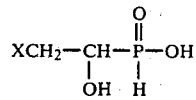

wherein X is a chlorine atom or a bromine atom, or its salt, which is useful as a fungicide.

19 Claims, No Drawings

α-HYDROXY-β-HALOETHYLPHOSPHINIC ACIDS AND THEIR SALTS, AND THEIR PRODUCTION AND USE

The present invention relates to α-hydroxy-β-haloethylphosphinic acids and their salts, and their production and use.

The α-hydroxy-β-haloethylphosphinic acids are represented by the formula:

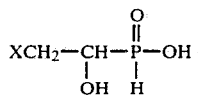  (I)

wherein X is a chlorine atom or a bromine atom.

Various fungicides having only a preventive effect have been used for control of plant diseases such as late blight and downy mildew which are caused by infection of Phycomycetes. However, their practical use was limited, since a sufficient controlling effect is not produced after the invasion of pathogenic fungi into plant bodies.

It has now been found that the α-hydroxy-β-haloethylphosphinic acids (I) and their salts such as metal salts and quaternary ammonium salts exhibit not only a preventive effect but also a curative effect against plant diseases such as late blight and downy mildew caused by infection of Phycomycetes. Thus, they are useful as fungicides for plants.

Examples of phytopathogenic fungi belonging to Phycomycetes, against which the α-hydroxy-β-haloethylphosphinic acids (I) and their salts can exert their fungicidal activity, are as follows: *Peronospora brassicae* on vegetables and radish, *Peronospora spinaciae* on spinach, *Peronospora tabacina* on tobacco, *Pseudoperonospora cubensis* on cucumber, *Plasmopara viticola* on grape, *Plasmopara nivea* on Umbelliferae plants, *Phytophthora cactorum* on apple, strawberry and carrot, *Phytophthora capsici* on tomato and cucumber, *Phytophthora cinnamomi* on pineapple, *Phytophthora infestans* on potato, tomato and eggplant, *Phytophthora nicotianae* var. *nicotianae* on tobacco, kidney bean and onion, *Pythium aphanidermatum* on cucumber, Pythium sp. on spinach, Pythium sp. on wheat, *Pythium debaryanum* on tobacco, Pythium rot (i.e. *P. aphanidermatum, P. debaryanum, P. irregulare, P. myriotylum, P. ultimum*) on soybean and so forth.

Accordingly, the α-hydroxy-β-haloethylphosphinic acids (I) and their salts may be used as fungicides applicable to plowed fields, orchards, tea-garden, mulberry garden, meadow, lawn and so on.

The α-hydroxy-β-haloethylphosphinic acid (I) is an acidic substance and can be produced by reacting a haloacetaldehyde of the formula:

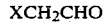  (II)

wherein X is as defined above or its dialkylacetal of the formula:

  (III)

wherein R is a lower alkyl group and X is as defined above with aqueous phosphinic acid in the presence of an acid catalyst (e.g. hydrochloric acid, sulfuric acid), usually at a temperature of 10° to 100° C. for 1 to 24 hours. The amount of the phosphinic acid may be 1.0 to 10 equivalents to the haloacetaldehyde (II) or its dialkylacetal (III).

When the α-hydroxy-β-haloethylphosphinic acid (I) is reacted with an organic or inorganic base or a metal salt in an inert solvent such as water, an alcohol (e.g. methanol, ethanol), an ether (e.g. tetrahydrofuran, dioxane) or a halogenated hydrocarbon (e.g. chloroform, dichloromethane), there is prepared its salt. This salt may be further subjected to salt-exchange with any metal salt in an inert solvent such as water or an alcohol (e.g. methanol, ethanol) to give any other salt. Alternatively, the α-hydroxy-β-haloethylphosphinic acid (I) may be treated with a cation exchange resin previously exchanged with an organic amine residue or a metal ion to give the corresponding salt.

Examples of the organic base are alkylamines (e.g. methylamine, ethylamine, n-propylamine, isopropylamine, n-butylamine, isobutylamine, sec-butylamine, tert-butylamine, n-amylamine, isoamylamine, n-hexylamine, cyclohexylamine, 2-methylpentylamine), alkenylamines (e.g. allylamine), aralkylamines (e.g. benzylamine, α-phenethylamine, β-phenethylamine, α-naphthylethylamine, α,α-dimethylbenzylamine, p-tolylphenylethylamine), heterocyclic ring-substituted alkylamines (e.g. 2-(2-thienyl)ethylamine, 2-(2-furyl)ethylamine, furfurylamine, 2-thienylmethylamine), dialkylamines (e.g. dimethylamine, diethylamine, methylethylamine, di-n-propylamine, diisopropylamine, di-n-butylamine, diisobutylamine), dialkenylamines (e.g. diallylamine), alkyl-aralkylamine (e.g. methyl-benzylamine, methylphenethylamine), trialkylamines (e.g. triethylamine, trimethylamine, tri-n-propylamine, tri-n-butylamine, dimethylcyclohexylamine), cyclic amines (e.g. pyrrolidine, piperidine, morpholine, 2-methylpiperidine, 2,6-dimethylmorpholine, piperazine, 4-methylpiperazine, triethylenediamine), alcohol amines (e.g. ethanolamine, N-methylethanolamine, N-isopropylethanolamine, N,N-dimethylethanolamine, diethanolamine, triethanolamine, tris(hydroxymethyl)aminomethane, diglycolamine), alkylenediamines (e.g. ethylenediamine, trimethylenediamine, N,N-dimethylethylenediamine, N,N'-dimethylethylenediamine, N,N,N',N'-tetramethylethylenediamine, N,N-dimethyltrimethylenediamine, N,N,N',N'-tetramethyltrimethylenediamine, 1,2-diaminocyclohexane, N,N-dimethyl-1,2-diaminocyclohexane), hydrazines (e.g. N-methylhydrazine, N,N-dimethylhydrazine, N-phenylhydrazine, N-3-acetylphenylhydrazine), anilines (e.g. aniline, N-methylaniline, diphenylamine, 4-fluoroaniline, 4-chloroaniline, 4-bromoaniline, 4-iodoaniline, 2,4-dichloroaniline, 2,5-dichloroaniline, 3,5-dichloroaniline, 2,4,6-trichloroaniline, 3-trifluoromethylaniline, 4-nitroaniline, 2-methyl-4-methoxyaniline, 3-fluoroaniline, 3-chloroaniline, 3-bromoaniline, 3-iodoaniline, 2,6-dimethylaniline, 2,6-diethylaniline, 4-methylaniline, 4-tert-butylaniline), nitrogen-containing heterocyclic bases (e.g. pyridine, α-picoline, β-picoline, γ-picoline, 2,6-lutidine, collidine, 2-amino-3-methylpyridine, 2,2'-bipyridyl, 4,4'-bipyridyl, 2,4'-bipyridyl, pyrazole, triazole, imidazole, triazine, pirazine, pyrimidine, thiazole, oxazole, isoxazole, quinoline, isoquinoline, pyrrole), etc. Examples of the inorganic base are alkali metal hydroxides (e.g. lithium hydroxide, sodium hydroxide, potassium hydroxide), ammonia, hydrazine, etc.

Examples of the metal salt are carbonates (e.g. calcium(II) carbonate, barium(II) carbonate, thallium(I) carbonate), acetates (e.g. zinc(II) acetate, calcium(II)

acetate, barium(II) acetate, magnesium(II) acetate, manganese(II) acetate, nickel(II) acetate, cobalt(II) acetate, copper(II) acetate), nitrates (e.g. calcium(II) nitrate, barium(II) nitrate, magnesium(II) nitrate, aluminum-(III) nitrate, manganese(II) nitrate, iron(III) nitrate, zinc(II) nitrate, nickel(II) nitrate, copper(II) nitrate, cobalt(II) nitrate), chlorides (e.g. calcium(II) chloride, barium(II) chloride, magnesium(II) chloride, iron(II) chloride, iron(III) chloride, zinc(II) chloride, tin(II) chloride, tin(IV) chloride, nickel(II) chloride, copper(II) chloride, cobalt(II) chloride, titanium(IV) chloride), lactates (e.g. aluminum(III) lactate), etc.

Some typical examples of the production of the $\alpha$-hydroxy-$\beta$-haloethylphosphinic acids (I) and their salts are shown in the following examples.

EXAMPLE 1

A solution of chloroacetaldehyde dimethylacetal (124.5 g) in phosphinic acid (50%, 132 g) was heated at 50° to 60° C. for 26 hours in the presence of concentrated hydrochloric acid (10 ml). The resultant mixture was concentrated in vacuo to give 140 g (96.7%) of $\alpha$-hydroxy-$\beta$-chloroethylphosphinic acid (Compound No. 1). $n_D^{22.0}$ 1.4970.

EXAMPLE 2

A solution of bromoacetaldehyde diethylacetal (197 g) in phosphinic acid (50%, 132.0 g) was heated at 60° to 70° C. for 48 hours in the presence of sulfuric acid (0.5 g). The resultant mixture was concentrated in vacuo to give 187.0 g (98.9%) of $\alpha$-hydroxy-$\beta$-bromoethylphosphinic acid (Compound No. 2). $n_D^{23}$ 1.5105.

EXAMPLE 3

To a solution of $\alpha$-hydroxy-$\beta$-chloroethylphosphinic acid (1.45 g) in water (12 ml), a solution of sodium hydroxide (0.4 g) in water (5 ml) was added, followed by stirring for 1 hour. The reaction mixture was concentrated in vacuo to give 1.67 g (99.8%) of sodium $\alpha$-hydroxy-$\beta$-chloroethylphosphinate (Compound No. 4) as a hygroscopic solid.

EXAMPLE 4

To a solution of aluminum lactate (50 g) in distilled water (1800 ml), weakly acidic cation exchange resin (Dowex CCR-2 H$^+$ type; 250 g) was added, and the resulting mixture was stirred for 1 hour. The resultant mixture was allowed to stand, and the supernatant was eliminated. To the residue, distilled water (500 ml) was added, and the resulting mixture was stirred for 30 minutes and then filtered. The resin was washed with distilled water and added to a solution of $\alpha$-hydroxy-$\beta$-bromoethylphosphinic acid (9.5 g) in water (150 ml), followed by stirring for 1 hour. The resulting mixture was filtered, and the collected resin was washed with distilled water. The filtrate was concentrated to give 9.8 g (90.7%) of aluminum $\alpha$-hydroxy-$\beta$-bromoethylphosphinate (Compound No. 11) as a white powder.

EXAMPLE 5

To a solution of $\alpha$-hydroxy-$\beta$-chloroethylphosphinic acid (1.45 g) in methanol (10 ml), a solution of morpholine (0.87 g) in methanol (10 ml) was added, and the resultant mixture was stirred for 2 hours. After removal of methanol by distillation, there was obtained 2.30 g (98%) of morpholinium $\alpha$-hydroxy-$\beta$-chloroethylphosphinate (Compound No. 12) as a creamy solid.

Some examples of the $\alpha$-hydroxy-$\beta$-haloethylphosphinic acids (I) and their salts are shown in Table 1.

TABLE 1

| Compound No. | Structure | Physical property |
|---|---|---|
| 1 | ClCH$_2$—CH(OH)—P(=O)(H)—OH | $n_D^{22}$ 1.4970 |
| 2 | BrCH$_2$—CH(OH)—P(=O)(H)—OH | $n_D^{23}$ 1.5105 |
| 3 | ClCH$_2$—CH(OH)—P(=O)(H)—ONH$_4$ | Hygroscopic solid |
| 4 | ClCH$_2$—CH(OH)—P(=O)(H)—ONa | Hygroscopic solid |
| 5 | ClCH$_2$—CH(OH)—P(=O)(H)—OLi | Hygroscopic solid |
| 6 | [ClCH$_2$—CH(OH)—P(=O)(H)—O]$_2$Ca | White powder |
| 7 | [ClCH$_2$—CH(OH)—P(=O)(H)—O]$_3$Al | White powder |
| 8 | BrCH$_2$—CH(OH)—P(=O)(H)—ONa | Hygroscopic solid |
| 9 | BrCH$_2$—CH(OH)—P(=O)(H)—ONH$_4$ | Hygroscopic solid |
| 10 | [BrCH$_2$—CH(OH)—P(=O)(H)—O]$_2$Ca | White powder |
| 11 | [BrCH$_2$—CH(OH)—P(=O)(H)—O]$_3$Al | White powder |
| 12 | ClCH$_2$—CH(OH)—P(=O)(H)—OH$_2$N(morpholine) | Creamy solid |

TABLE 1-continued

| Compound No. | Structure | Physical property |
|---|---|---|
| 13 | ClCH$_2$—CH(OH)—P(=O)(OH)—OH$_3$NC$_4$H$_9$(t) | M.P. 149–151° C. |
| 14 | BrCH$_2$—CH(OH)—P(=O)(H)—OHN(C$_2$H$_5$)$_3$ | Creamy solid |
| 15 | ClCH$_2$—CH(OH)—P(=O)(H)—OH$_3$NC$_3$H$_7$(iso) | $n_D^{24}$ 1.4750 |
| 16 | ClCH$_2$—CH(OH)—P(=O)(H)—OHN(C$_2$H$_5$)$_3$ | $n_D^{24}$ 1.4780 |
| 17 | ClCH$_2$—CH(OH)—P(=O)(H)—OH$_2$N(CH$_3$)$_2$ | Creamy solid |
| 18 | ClCH$_2$—CH(OH)—P(=O)(H)—OH$_3$NC$_2$H$_5$ | $n_D^{24}$ 1.4735 |
| 19 | BrCH$_2$—CH(OH)—P(=O)(H)—OH$_2$N⟨C$_5$H$_{10}$⟩ | Creamy solid |
| 20 | BrCH$_2$—CH(OH)—P(=O)(H)—OH$_2$N⟨C$_4$H$_8$O⟩ | Creamy solid |

In their actual application as fungicides, the α-hydroxy-β-haloethylphosphinic acids (I) and their salts may be used alone without the incorporation of other ingredients. For easier application, however, they are normally employed in admixtue with solid or liquid carriers or diluents. The fungicidal compositions can be formulated into any of ordinarily adopted forms such as, for example, dusts, granules, wettable powders, emulsifiable concentrates, fine particles, aqueous solutions, oil sprays, aerosols and tablets. Such compositions generally contain 0.1 to 99.9% by weight, preferably 2.0 to 80.0% by weight of the active ingredient.

As the solid carriers or diluents usable for formulation of the fungicidal composition, there may be exemplified plant carriers (e.g. wheat flour, tobacco powder, soybean powder, walnut-shell powder, wooden powder, saw dust, wheat bran, bark dust, cellulose powder, extract residue), fibrous products (e.g. paper, card board, rag), crushed synthetic resins, clays (e.g. kaolin, bentonite, terra alba), talcs, other inorganic minerals (e.g. pyrophyllite, celicite, pumice, sulfur powder, diatomaceous earth, white carbon, activated carbon), chemical fertilizers (e.g. ammonium sulfate, ammonium phosphate, ammonium nitrate, urea, ammonium chloride), etc. As the liquid carriers or diluents, there may be employed water, alcohols (e.g. methanol, ethanol), ketones (e.g. acetone, methylethylketone), ethers (e.g. diethyl ether, dioxane, cellosolve, tetrahydrofuran), aromatic hydrocarbons (e.g. benzene, toluene, xylene, methylnaphthalene), aliphatic hydrocarbons (e.g. gasoline, kerosene, lamp oil), esters, nitriles, acid amides (e.g. methylformamide, dimethylacetamide), halogenated hydrocarbons (e.g. dichloroethane, trichloroethylene, carbon tetrachloride), etc.

In addition to the solid or liquid carriers or diluents as exemplified above, there may be used surfactants when desired. Examples of the surfactants are polyoxyethylene phenylphenol polymer, polyoxyethylene alkylaryl ether, sodium laurylsulfate, calcium alkylbenzenesulfonate, alkylsulfates, alkylsulfonates, alkylarylsulfonates, polyethyleneglycol ethers, polyvalent alcohol esters, etc. There may be also used adhesive agents, dispersing agents, stabilizers, etc. Their specific examples are casein, gelatin, starch, carboxymethyl cellulose, gum arabic, alginate, calcium ligninsulfonate, bentonite, molasse, polyvinyl alcohol, palm oil, agar, acid isopropyl phosphate, tricresyl phosphate, tall oil, epoxylated oil, surfactants, aliphatic acids and their esters, etc.

Moreover, the fungicidal composition may comprise other fungicides, insecticides, nematocides, acaricides, insect repellents, plant growth regulators, herbicides, fertilizers, soil improvers, etc.

Some typical examples of the fungicidal composition of this invention are shown below. In those examples, part(s) and % are by weight unless otherwise indicated.

EXAMPLE A

Compound No. 13 (2 parts), clay (88 parts) and talc (10 parts) are thoroughly pulverized and mixed together to obtain a dust containing 2% of the active ingredient.

EXAMPLE B

Compound No. 6 (30 parts), diatomaceous earth (45 parts), white carbon (20 parts), a wetting agent (sodium laurylsulfate) (3 parts) and a dispersing agent (calcium ligninsulfonate) (2 parts) are thoroughly pulverized and mixed together to obtain a wettable powder containing 30% of the active ingredient.

EXAMPLE C

Compound No. 7 (50 parts), diatomaceous earth (45 parts), a wetting agent (calcium alkylbenzenesulfonate) (2.5 parts) and a dispersing agent (calcium ligninsulfonate) (2.5 parts) are thoroughly pulverized and mixed together to obtain a wettable powder containing B 50% of the active ingredient.

EXAMPLE D

Compound No. 13 (20 parts), xylene (60 parts) and an emulsifier (polyoxyethylene phenylphenol polymer type) (20 parts) are mixed together to obtain an emulsifiable concentrate containing 20% of the active ingredient.

EXAMPLE E

Compound No. 10 (50 parts), water (45 parts) and a wetting agent (polyoxyethylene alkylaryl ether type) (5 parts) are mixed together to obtain an aqueous solution containing 50% of the active ingredient.

A suitable amount of the fungicidal composition of the invention to be applied is generally from 10 to 200 grams in terms of the active ingredient per 10 are. In case of a composition form such as a wettable powder, emulsifiable concentrate or aqueous solution, it is normally diluted with water and then applied. The concentration of the active ingredient on the application is preferably within the range of 0.001 to 0.2% by weight. In case of a composition form such as a dust or granule, it is ordinarily applied as such. Since, however, the amount and concentration largely depend upon composition forms, application times, application methods, application sites, diseases and crops, they may be increased or decreased appropriately.

The following examples show some typical test results supporting the excellent fungicidal activity of the α-hydroxy-β-haloethylphosphinic acids (I) and their salts. In these examples, the compound numbers correspond to those in Table 1. The compounds used for comparison are as follows:

| Compound No. | Structure | Remarks |
|---|---|---|
| A | (tetrachloroisophthalonitrile: Cl₄-benzene with 2 CN groups) | Commercially available fungicide "chlorothalonil" |
| B | $\left( \begin{array}{c} CH_3CH_2O \\ \phantom{x} \\ H \end{array} \underset{\phantom{x}}{\overset{\displaystyle O}{\underset{\displaystyle O}{P}}} \right)_3 Al$ | Commercially available fungicide "efosite-aluminium" |
| C | $\begin{array}{c} CH_2-NH-CS-S \\ \phantom{xxxxxxxxx} \searrow \\ \phantom{xxxxxxxxxxxxx} Zn \\ \phantom{xxxxxxxxx} \nearrow \\ CH_2-NH-CS-S \end{array}$ | Commercially available fungicide "zineb" |
| D | $\begin{array}{c} CH_2-NH-CS-S \\ \phantom{xxxxxxxxx} \searrow \\ \phantom{xxxxxxxxxxxxx} Mn \\ \phantom{xxxxxxxxx} \nearrow \\ CH_2-NH-CS-S \end{array}$ | Commercially available fungicide "maneb" |

EXAMPLE I

Seeds of cucumber (species: "Sagamihanjiro") were sowed in soil filled in plastic pots and cultivated in a greenhouse for 14 days to obtain seedlings of cucumber having cotyledons. An aqueous dilution of the test compound in the form of aqueous solution or wettable powder was applied onto the seedlings by foliar treatment. Then, the seedlings were grown in the greenhouse for 5 days. A spore suspension of *Pseudoperonospora cubensis* was sprayed onto the seedlings, which were placed at 20° C. under a humid condition for 3 days and then grown at 20° C. under the irradiation with a fluorescent lamp for 3 days. The state of infection of the test plants was observed, and the preventive value was calculated according to the following equation:

| Infection index | State of infection |
|---|---|
| 0 | No infectious spot on leaf |
| 0.5 | Infectious spots of less than 5% of the area of leaf |
| 1 | Infectious spots of less than 20% of the area of leaf |
| 2 | Infectious spots of less than |

| Infection index | State of infection |
|---|---|
| 4 | 50% of the area of leaf Infectious spots of not less than 50% of the area of leaf |

$$\text{Degree of infection (\%)} = \frac{\Sigma\{(\text{Infection index}) \times (\text{number of leaves})\}}{(\text{Total number of leaves}) \times 4} \times 100$$

$$\text{Preventive value (\%)} = 100 - \frac{(\text{Degree of infection in medicated plot})}{(\text{Degree of infection in non-medicated plot})} \times 100$$

The results are shown in Table 2.

TABLE 2

| Compound No. | Concentration of active ingredient (ppm) | Preventive value (%) |
|---|---|---|
| 1 | 200 | 100 |
| 2 | 200 | 100 |
| 3 | 200 | 100 |
| 4 | 200 | 100 |
| 5 | 200 | 100 |
| 6 | 200 | 100 |
| 7 | 200 | 100 |
| 8 | 200 | 100 |
| 9 | 200 | 95 |
| 10 | 200 | 90 |
| 11 | 200 | 75 |
| 12 | 200 | 100 |
| 13 | 200 | 100 |
| 14 | 200 | 100 |
| 15 | 200 | 100 |
| 16 | 200 | 100 |
| 17 | 200 | 100 |
| 18 | 200 | 100 |
| 19 | 200 | 85 |
| 20 | 200 | 100 |
| B | 200 | 44 |

EXAMPLE II

Seeds of cucumber (species: "*sagamihanjiro*") were sowed in soil filled in plastic pots and cultivated in a greenhouse for 14 days to obtain seedlings of cucumber having cotyledons. The seedlings were treated by soil-drench with an aqueous dilution of the test compound in the form of aqueous solution or wettable powder. After 4 days, a spore suspension of *Pseudoperonospora cubensis* was sprayed onto the seedlings, which were placed at 20° C. under a humid condition for 3 day and then grown at 20° C. under the irradiation with a fluorescent lamp for 4 days. The state of infection of the plants was observed, and the preventive value was calculated as in Example I.

The results are shown in Table 3.

TABLE 3

| Compound No. | Amount of active ingredient (g/are) | Preventive value (%) |
|---|---|---|
| 1 | 100 | 100 |
| 2 | 100 | 100 |
| 3 | 100 | 100 |
| 4 | 100 | 100 |
| 5 | 100 | 100 |
| 6 | 100 | 100 |
| 7 | 100 | 100 |
| 8 | 100 | 100 |
| 9 | 100 | 100 |
| 10 | 100 | 100 |
| 11 | 100 | 100 |
| 12 | 100 | 100 |
| 13 | 100 | 100 |

TABLE 3-continued

| Compound No. | Amount of active ingredient (g/are) | Preventive value (%) |
|---|---|---|
| 14 | 100 | 100 |
| 15 | 100 | 100 |
| 16 | 100 | 100 |
| 17 | 100 | 100 |
| 18 | 100 | 100 |
| 19 | 100 | 100 |
| 20 | 100 | 100 |
| A | 100 | 0 |
| B | 100 | 25 |

EXAMPLE III

Seeds of grape (species: "delaware") were sowed in soil filled in plastic pots and cultivated in a greenhouse for 2 months to obtain seedlings of grape at the 2 to 3-leaved stage. A spore suspension of Plasmopara viticola was sprayed onto the seedlings, which were placed at 23° C. under a humid condition for 2 days. Then, an aqueous dilution of the test compound in the form of aqueous solution or wettable powder was applied onto the seedlings by foliar treatment. Thereafter, the seedlings were grown at 23° C. under the irradiation with a fluorescent lamp for 14 days. The state of infection of the plants was observed, and the preventive value was calculated as in Example I.

The results are shown in Table 4.

TABLE 4

| Compound No. | Concentration of active ingredient (ppm) | Preventive value (%) |
|---|---|---|
| 1 | 500 | 100 |
| 2 | 500 | 100 |
| 3 | 500 | 100 |
| 4 | 500 | 100 |
| 5 | 500 | 100 |
| 6 | 500 | 100 |
| 7 | 500 | 100 |
| 8 | 500 | 100 |
| 9 | 500 | 100 |
| 10 | 500 | 100 |
| 11 | 500 | 100 |
| 12 | 500 | 100 |
| 13 | 500 | 100 |
| 14 | 500 | 100 |
| 15 | 500 | 100 |
| 16 | 500 | 100 |
| 17 | 500 | 100 |
| 18 | 500 | 100 |
| 19 | 500 | 100 |
| 20 | 500 | 100 |
| A | 500 | 69 |
| B | 1000 | 0 |

EXAMPLE IV

Seeds of potato (species: "danshaku") were sowed in soil filled in plastic pots and cultivated in a greenhouse for 2 months to obtain seedlings of potato. A spore suspension of Phytophthora infestans was sprayed onto the seedlings, which were placed at 20° C. under a humid condition for 20 hours. Then, an aqueous dilution of the test compound in the form of aqueous solution or wettable powder was applied onto the seedlings by foliar treatment. Thereafter, the seedlings were grown at 15° C. under a humid condition for 6 days. The state of infection of the plants was observed, and the preventive value was calculated as in Example I.

The results are shown in Table 5.

TABLE 5

| Compound No. | Concentration of active ingredient (ppm) | Preventive value (%) |
|---|---|---|
| 1 | 500 | 83 |
| 2 | 500 | 92 |
| 6 | 500 | 97 |
| 7 | 500 | 91 |
| 8 | 500 | 86 |
| 9 | 500 | 78 |
| 10 | 500 | 95 |
| D | 1000 | 0 |

What is claimed is:

1. A compound of the formula:

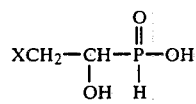

wherein X is a chlorine atom or a bromine atom, or an organic or an inorganic base or metal salt thereof.

2. The compound according to claim 1, which is in the form of a calcium salt.

3. The compound according to claim 1, which is in the form of an aluminium salt.

4. The compound according to claim 1, which is in the form of an ammonium salt.

5. The compound according to claim 1, wherein the organic base is a member selected from the group consisting of alkylamines, alkenylamines, aralkylamines, heterocyclic ring-substituted alkylamines, dialkylamines, dialkenylamines, alkylaralkylamines, trialkylamines, cyclic amines, alcholamines, alkylenediamines, hydrazines, anilines, and nitrogen-containing heterocyclic bases.

6. The compound according to claim 1, wherein the inorganic base is a member selected from the group consisting of alkali metal hydroxides, ammonia, and hydrazine.

7. The compound according to claim 1, wherein the metal salt is a member selected from the group consisting of metal carbonates, metal acetates, metal nitrates, metal chlorides and metal lactates.

8. A compound selected from the group consisting of α-hydroxy-β-chloroethylphosphinic acid, α-hydroxy-β-bromoethylphosphinic acid, ammonium α-hydroxy-β-chloroethylphosphinate, sodium α-hydroxy-β-chloroethylphosphinate, lithium α-hydroxy-β-chloroethylphosphinate, calcium α-hydroxy-β-chloroethylphosphinate, aluminum α-hydroxy-β-chloroethylphosphinate, sodium α-hydroxy-β-bromoethylphosphinate, ammonium α-hydroxy-β-bromoethylphosphinate, calcium α-hydroxy-β-bromoethylphosphinate, aluminum α-hydroxy-β-bromoethylphosphinate, morpholinium α-hydroxy-β-chloroethylphosphinate, t-butylammonium α-hydroxy-β-chloroethylphosphinate, triethylammonium α-hydroxy-β-bromoethylphosphinate, isopropylammonium α-hydroxy-β-chloroethylphosphinate, triethylammonium α-hydroxy-β-chloroethylphosphinate, dimethylammonium α-hydroxy-β-chloroethylphosphinate, ethylammonium α-hydroxy-β-chloroethylphosphinate, piperidinium α-hydroxy-β-bromoethylphosphinate and morpholinium α-hydroxy-β-bromoethylphosphinate.

9. A process for producing the compound according to claim 1, which comprises reacting a haloacetaldehyde dialkylacetal of the formula:

XCH₂CH(OR)₂ wherein R is a lower alkyl group and X is a chlorine or bromine atom with aqueous phosphinic acid in the presence of an acid catalyst.

10. The process according to claim 9, wherein the α-hydroxy-β-haloethylphosphinic acid is reacted with an organic or inorganic base or a metal salt.

11. A fungicidal composition which comprises as an active ingredient a fungicidally effective amount of the compound according to claim 1, and an inert carrier or diluent.

12. The composition according to claim 11, wherein the concentration of the active ingredient is 0.1 to 99.9% by weight.

13. The composition according to claim 12, wherein the concentration of the active ingredient is 2.0 to 80.0% by weight.

14. A fungicidal composition which comprises as an active ingredient a fungicidally effective amount of a compound according to claim 8, and an inert carrier or diluent.

15. A method for preventing a plant disease which comprises applying a fungicidally effective amount of the compound according to claim 1 to plants.

16. The method according to claim 15, wherein the plant disease is the one caused by fungi belonging to Phycomycetes.

17. A method for curing a plant disease which comprises applying a fungicidally effective amount of the compound according to claim 1 to diseased plants.

18. The method according to claim 17, wherein the plant disease is the one caused by fungi belonging to Phycomycetes.

19. A method for preventing a plant disease which comprises applying a fungicidally effective amount of a compound according to claim 8.

* * * * *